United States Patent
Nakamura et al.

(10) Patent No.: US 11,826,131 B2
(45) Date of Patent: Nov. 28, 2023

(54) VAGINA EVALUATION DEVICE AND UTERUS EVALUATION DEVICE

(71) Applicant: OSAKA UNIVERSITY, Suita (JP)

(72) Inventors: Hitomi Nakamura, Suita (JP); Tadashi Kimura, Suita (JP); Takayoshi Hosono, Neyagawa (JP)

(73) Assignee: OSAKA UNIVERSITY, Suita (JP)

( * ) Notice: Subject to any disclaimer, the term of this patent is extended or adjusted under 35 U.S.C. 154(b) by 543 days.

(21) Appl. No.: 16/776,631

(22) Filed: Jan. 30, 2020

(65) Prior Publication Data

US 2020/0163579 A1     May 28, 2020

Related U.S. Application Data

(62) Division of application No. 16/250,564, filed on Jan. 17, 2019, now Pat. No. 10,602,955, which is a
(Continued)

(30) Foreign Application Priority Data

Mar. 28, 2014   (JP) ................................ 2014-067934

(51) Int. Cl.
    *A61B 5/0538*     (2021.01)
    *A61B 5/00*     (2006.01)
    (Continued)

(52) U.S. Cl.
    CPC ............ *A61B 5/0538* (2013.01); *A61B 5/053* (2013.01); *A61B 5/4325* (2013.01);
    (Continued)

(58) Field of Classification Search
    CPC . A61B 10/0012; A61B 5/6875; A61B 5/6853; A61B 5/4337; A61B 5/4331;
    (Continued)

(56) References Cited

U.S. PATENT DOCUMENTS 4,224,949 A   *   9/1980   Scott .................. A61B 10/0012
                                                                    600/551
4,396,019 A      8/1983   Perry, Jr.
(Continued)

FOREIGN PATENT DOCUMENTS

DE         3900178 A   *   7/1990   ......... A61B 5/0421
JP         H1183797 A   *   3/1999
(Continued)

OTHER PUBLICATIONS

Int'l Search Report dated Jun. 16, 2015 in Int'l Application No. PCT/JP2015/001708.
(Continued)

*Primary Examiner* — Ashley K Buran
*Assistant Examiner* — Helene Bor
(74) *Attorney, Agent, or Firm* — Panitch Schwarze Belisario & Nadel LLP

(57) ABSTRACT

A non-invasive and accurate vagina evaluation device and uterine evaluation devices are provided that measure the receptivity (uterine implantation capacity) of the mother's body to a fertilized egg implanting itself into the uterus. A first vagina evaluation device includes: a main body stretchable and expandable after insertion into a vagina, followed by air injection thereinto; four electrodes brought into contact with the vagina wall as the main body expands and stretches; and fixation means configured to fix the interval of arrangement of the electrodes. Second and third uterine evaluation device include: a flexible and rod-shaped main body for insertion into a uterine cavity; and four or two impedance electrodes arranged with a predetermined interval therebetween in an insertion direction of the main body and brought into contact with an endometrium of the uterine cavity to measure a uterine endometrial impedance generated between the endometrium and each of the electrodes.

4 Claims, 6 Drawing Sheets

Related U.S. Application Data division of application No. 15/129,783, filed as application No. PCT/JP2015/001708 on Mar. 25, 2015, now Pat. No. 10,271,760.

(51) Int. Cl.
*A61B 5/053* (2021.01)
*A61B 10/00* (2006.01)

(52) U.S. Cl.
CPC .......... *A61B 5/4331* (2013.01); *A61B 5/4337* (2013.01); *A61B 5/6853* (2013.01); *A61B 5/6875* (2013.01); *A61B 10/0012* (2013.01); *A61B 2010/0016* (2013.01)

(58) Field of Classification Search
CPC ..... A61B 5/4325; A61B 5/053; A61B 5/0538; A61B 2010/0016
See application file for complete search history.

(56) References Cited

U.S. PATENT DOCUMENTS

| | | | |
|---|---|---|---|
| 4,498,481 A * | 2/1985 | Lemke | A61D 17/002 600/549 |
| 4,753,247 A * | 6/1988 | Kirsner | A61B 10/0012 324/692 |
| 5,010,895 A | 4/1991 | Maurer et al. | |
| 5,154,177 A | 10/1992 | Eisman et al. | |
| 5,240,010 A * | 8/1993 | Weinmann | A61B 10/0012 600/551 |
| 5,662,699 A | 9/1997 | Hamedi et al. | |
| 6,269,261 B1 * | 7/2001 | Ootomo | A61B 5/14542 600/584 |
| 6,360,123 B1 | 3/2002 | Kimchi et al. | |
| 6,391,024 B1 | 5/2002 | Sun et al. | |
| 7,582,085 B2 | 9/2009 | Bowman et al. | |
| 7,905,880 B2 | 3/2011 | Harrington et al. | |
| 8,060,195 B2 | 11/2011 | Gurewitsch et al. | |
| 8,600,471 B2 * | 12/2013 | Wadhawan | A61B 5/416 600/361 |
| 2001/0014804 A1 * | 8/2001 | Goble | A61B 18/1492 606/41 |
| 2004/0132556 A1 | 7/2004 | Jacome | |
| 2014/0005509 A1 * | 1/2014 | Bhavaraju | A61B 5/1473 600/347 |
| 2018/0036072 A1 | 2/2018 | Mathur et al. | |

FOREIGN PATENT DOCUMENTS

| | | | | |
|---|---|---|---|---|
| UA | 53133 U | * | 9/2010 | |
| WO | 2012070569 A1 | | 5/2012 | |
| WO | WO2012070569 | * | 5/2012 | ......... A61B 10/0012 |

OTHER PUBLICATIONS

Int'l Preliminary Report on Patentability dated Oct. 13, 2016 in Int'l Application No. PCT/JP2015/001708.
Office Action dated Jul. 27, 2018 in U.S. Appl. No. 15/129,783 by Nakamura.
Office Action dated Sep. 13, 2019 in U.S. Appl. No. 16/250,564 by Nakamura.

* cited by examiner

| Probe | Interval Between Electrodes: L3 | Substantial Difference |
|---|---|---|
| A | 3 mm | Positive |
| B | 1 mm | Positive |
| C | 6 mm | Positive |
| D | 6 mm | Positive |
| E | 6.5 mm | Positive |
| F | 7.5 mm | Negative |

VAGINA EVALUATION DEVICE AND UTERUS EVALUATION DEVICE

CROSS-REFERENCE TO RELATED APPLICATION

This application is a Divisional of co-pending U.S. patent application Ser. No. 16/250,564, filed Jan. 17, 2019, which is a Divisional of U.S. patent application Ser. No. 15/129,783, filed Sep. 27, 2016, which is a Section 371 of International Application No. PCT/JP2015/001708, filed Mar. 25, 2015, which was published in the Japanese language on Oct. 1, 2015, under International Publication No. WO 2015/146172 A1, which claims priority under 35 U.S.C. § 119 to Japanese Patent Application No. 2014-067934, filed on Mar. 28, 2014, the disclosures of which are incorporated herein by reference.

TECHNICAL FIELD

The present invention relates to vaginal and uterine evaluation devices and, in particular, vaginal and uterine evaluation devices that evaluate non-invasively the prospect of uterine condition whether the uterine endometrium will be able to prepare to receive fertilized egg to adhere and implant to uterine wall in this menstrual cycle (uterine receptivity).

BACKGROUND ART

In previous infertility treatment, recently, it is necessary to evaluate the prospect of uterine receptivity in each menstrual cycle. Uterine receptivity has been clinically estimated via (1) measurement of blood progesterone level, (2) measurement of the uterine endometrial thickness using ultrasonic diagnostic equipment, and (3) histological examination of a physically collected uterine endometrium. However, among the methods (1) to (3), the method (3) is invasive for the patient, and is unreliable for predicting the outcome of infertility treatment, and thus, remains to be controversial in clinical significance. Although methods (1) and (2) have been used in daily practice, they are not effective enough to evaluate the prospect of uterine receptivity.

Using human implantation failure model mice established by the Inventors (Nakamura, et al.) (Non patent literature 1), the Inventors found that the following parameters could evaluate the prospect of uterine receptivity (Patent literature 1);

a uterine endometrial impedance and an intravaginal impedance were effective parameters. For this purpose Patent literature 1 discloses the general shape of a device which can contact with the vaginal wall and a device which can make contact with the uterine wall and be inserted into uterine cavity to measure a uterine endometrial impedance or a uterine endometrial redox potential difference in real time to evaluate the prospect of uterine receptivity.

As described in Patent literature 1, to evaluate the uterine implantation capacity, it is important to measure the impedance and further, it is necessary to measure it accurately. As disclosed in Patent literature 1, to evaluate the prospect of uterine receptivity, these devices preferably have to be particular shapes to keep the electrodes in contact with the uterine wall or the vaginal wall and also to be inserted into the vagina or uterine cavity. However, Patent literature 1 did not mention the specific shape of the probe and arrangement of the electrodes and Patent literature 1 did not provide a method for how to keep the electrodes in contact with accurately with vaginal or uterine wall and a method of reducing the burden on the patient, which is important in the field of infertility treatment.

Consequently, in the field of infertility treatment, there is a demand for a medical equipment to evaluate the prospect of uterine receptivity vagina evaluation device or a uterus evaluation device that has specific shapes of vaginal and uterine probes with specific arrangement of electrodes which can accurately measure a uterine endometrial redox potential difference or uterine endometrial impedance in the uterine cavity, or a uterine endometrial impedance on the vagina wall, and can reduce the burden on the patient at the point of insertion of the probe into the vagina or the uterine cavity (accurate measurement and low invasiveness to the patients are highly demanded).

PRIOR ART LITERATURE

Patent Literature

Patent Literature 1: International Publication No. WO2012/070569

Non Patent Literature

Non Patent Literature FEBS Lett. 580 (11): 2717-2722

SUMMARY OF THE INVENTION

Technical Problem

The present invention has been devised in consideration of the above-mentioned problem, and intends to provide a vaginal evaluation devise capable of low-invasive and accurate measurement that can be inserted into the vagina safely and can keep the electrodes in contact with a vaginal or uterine wall properly. Further, the present invention also intends to provide a uterus evaluation device capable of low-invasive and accurate measurement that can be inserted into a uterine cavity safely to bring an electrode into contact with tissues in the uterine cavity.

Solutions to the Problem

The first aspect of the present invention provides a vaginal evaluation device for biological evaluation of a subject's vagina including: a main body (balloon 18 in this embodiment) stretchable and expandable in at least a vagina wall direction after insertion into a vagina by air injection thereinto; four electrodes arranged substantially in a line around the surface of the main body with a predetermined interval therebetween, the electrodes being brought into contact with the vagina wall as the main body expands and stretches; and a fixation means configured to fix the interval in the arrangement of the electrodes irrespective of expansion and stretching of the main body, wherein an impedance generated between each of the electrodes and the vagina wall is measured.

This vaginal evaluation device can be inserted into the vagina safely since the main body thereof not expand at the time of insertion into the vagina and, once inserted, the main body is expanded to a desired dimension by air after the insertion and the electrodes arranged on the surface of the main body can be brought into contact with the vaginal wall. The four electrodes are arranged substantially in a line, and the interval between the electrodes is fixed irrespective of expansion and stretching of the main body, achieving proper measurement according to a four-electrode method, which is mentioned below.

Preferably, at expansion of the main body, each of the electrodes protrudes from the surface of the main body toward the vaginal wall.

With this vagina evaluation device, the contact between the electrodes and vaginal wall is ensured because the electrodes are protruding toward the direction of the vagina wall.

Preferably, the tip of each of the electrodes on the side of the vaginal wall is substantially round shape.

Since the vaginal wall is also round shape from the view of inside of the vagina, the round shape tip of each electrode can sufficiently keep contact with the vaginal wall using this evaluation device. Further, the surface of the electrodes are smooth and this can solve the problem of invasiveness to the vaginal wall.

Preferably, the fixation means is a reinforcing member arranged on the surface of the main body in the vicinity of each of the electrodes.

With this vaginal evaluation device, the reinforcing member is arranged nearby each of the electrodes in order to allow the degradation of the expansion and stretching capability of the main body to be minimized and the proper interval between the electrodes can be kept regardless of the expansion and stretching of the main body.

It was found that the interval between the adjacent electrodes arranged substantially in a line was 6.0 mm.

The second aspect of the present invention provides a uterine evaluation device for biological evaluation of a subject's uterus including: a flexible and rod-shaped main body capable of being inserted into a uterine cavity and four impedance electrodes arranged with a predetermined interval therebetween in an insertion direction of the main body wherein the 4 electrodes can contact with the uterine cavity to measure uterine cavity impedance generated between the lining of the uterine cavity and each of the electrodes.

The second aspect of the present invention also provides a uterine evaluation device for biological evaluation of a subject's uterus including: a flexible and rod-shaped main body capable of being inserted into a uterine cavity and five electrodes arranged with a predetermined interval therebetween in an insertion direction of the main body that can contact with the uterine cavity, wherein the electrodes includes a redox potential difference electrode arranged at a tip of the main body in the insertion direction of the main body to measure a redox potential difference between the uterine cavity and a body surface, and four impedance electrodes arranged with a predetermined interval therebetween in the rear of the redox potential difference electrode in the insertion direction of the main body to measure a uterine endometrial impedance generated between the lining of the uterine cavity and each of the impedance electrodes.

In consideration of the characteristics of the uterine cavity, the main body of the uterine evaluation device is made by a flexible rod-shaped member and thus, can be safely inserted into the uterine cavity. Further, to be suitable for the four-electrode method, with the uterus evaluation device, the redox potential difference electrode and the four impedance electrodes are arranged substantially in a line in this order from the tip of the main body.

Preferably, each of the impedance electrodes is cingulum-shaped, and coats the main body around an axis of the main body.

Since the main body of this uterine evaluation device is coated with electrodes around the axis, the electrodes make sufficient contact with the uterine cavity regardless of the position and orientation of the main body in the uterine cavity. This particular form enables this uterine device to measure in-vivo uterine impedance in women accurately.

Preferably, the interval between the second and third impedance electrodes from the tip of the main body is a predetermined distance.

With this uterus evaluation device, the interval of the second and third impedance electrodes from the tip when viewed from the front end is fixed, which enables more accurate measurement of impedance by four-electrodes method as described below.

Preferably, from the tip of the main body the interval between the first and the second impedance electrodes and the interval between the third and fourth impedance electrodes are 4.0 mm, and the interval between the second and third electrode is 6.0 mm.

Preferably, a distance between the tip of the main body and the fourth impedance electrode is 50.0 mm or less.

The third aspect of the present invention provides a uterine evaluation device for biological evaluation of a subject's uterus including: a rod-shaped main body capable of being inserted into a uterine cavity; and
    two impedance electrodes arranged with a predetermined interval therebetween in an insertion direction of the main body, the impedance electrodes being brought into contact with a lining of the uterine cavity, to measure a uterine endometrial impedance generated between the lining of the uterine cavity and each of the impedance electrodes.

The third aspect of the present invention is also a uterine evaluation device for biological evaluation of a subject's uterus including:
    a rod-shaped main body capable of being inserted into a uterine cavity; and
    three electrodes arranged with a predetermined interval therebetween in an insertion direction of the main body, the electrodes being brought into contact with a lining of the uterine cavity,
    wherein the electrodes includes a redox potential difference electrode arranged at a tip of the main body in the insertion direction of the main body to measure a redox potential difference between the uterine cavity and a body surface, and two impedance electrodes arranged with a predetermined interval therebetween in the rear of the redox potential difference electrode in the insertion direction to measure a uterine endometrial impedance generated between the lining of the uterine cavity and each of the impedance electrodes.

This uterine evaluation device uses the two electrodes at measurement of the impedance according to the two-electrode method and thus, the device can be simply configured, achieving a high yield rate, and easy measurement at low costs. The four-electrode method has a low grounding resistance and a high measurement accuracy at measurement, while the two-electrode method enables measurement more readily at lower costs than the four-electrodes method.

Preferably, each of the impedance electrodes is cingulum-shaped, and coats the main body around an axis of the main body.

Since the main body of this uterine evaluation device is coated with electrodes around the axis, the electrodes make sufficient contact with the uterine wall regardless of the position and orientation of the main body in the uterine cavity. This particular form enables this uterine device to measure in-vivo uterine impedance in women accurately.

Preferably, the interval between the two electrodes arranged substantially in a line is 6.0 to 6.5 mm.

With this uterine evaluation device, the interval between the two electrodes for measuring the impedance is 1.0 to 6.5 mm, the difference between impedance values of mice at the day 2.5 and 4.5 post coitum (p.c.) in mice can be accurately measured, thereby evaluating the implantation progress with high accuracy.

With the uterus evaluation device, when the interval between the two electrodes for measuring the impedance is 6.0 to 7.5 mm, the difference between impedance values of the implantation failure model mice and that of control mice can be accurately measured, thereby evaluating implantation with high accuracy.

Therefore, when the interval between the two electrodes for measuring the impedance is 6.0 to 6.5 mm, this uterine evaluation device can accurately measure the difference between impedance values of at day 2.5 and 4.5 p.c. in mice, to evaluate the implantation progress with high accuracy, as well as the difference between impedance values of the implantation failure model mouse and the control mouse, to evaluate the implantation with high accuracy.

Advantageous Effects of the Invention

As described above, the vagina evaluation device from the first aspect of the present invention includes the main body expandable after insertion into the vagina, followed by air injection thereinto, and the electrodes arranged to be suitable for the four-electrode method, achieving low-invasive and accurate biological evaluation of the vagina, in particular, the implantation capacity. Further, since the tip of each electrode is substantially round shape, the electrodes make contact with the vagina wall sufficiently and safely, to enable low-invasive and accurate measurement. The uterus evaluation device from the second aspect of the present invention includes the flexible and rod-shaped main body capable of being safely inserted into the uterine cavity, and the electrodes arranged to be suitable for the four-electrode method, achieving low-invasive and accurate biological evaluation of the vagina, in particular, the implantation capacity, as in the vagina evaluation device from the first aspect of the present invention. Moreover, the cingulum-like electrodes coat the main body, enabling proper contact of the electrodes with the endometrium of the uterine cavity to achieve accurate measurement.

As described above, the third aspect of the present invention, the uterine evaluation device from the third aspect of the present invention uses the two electrodes at measurement of the impedance according to the two-electrode method. Thus, the uterus evaluation device can be simply configured, achieving a high yield rate, and evaluating the uterus, in particular, the implantation capacity readily at low costs.

EMBODIMENTS FOR CARRYING OUT INVENTION

Figure 1:
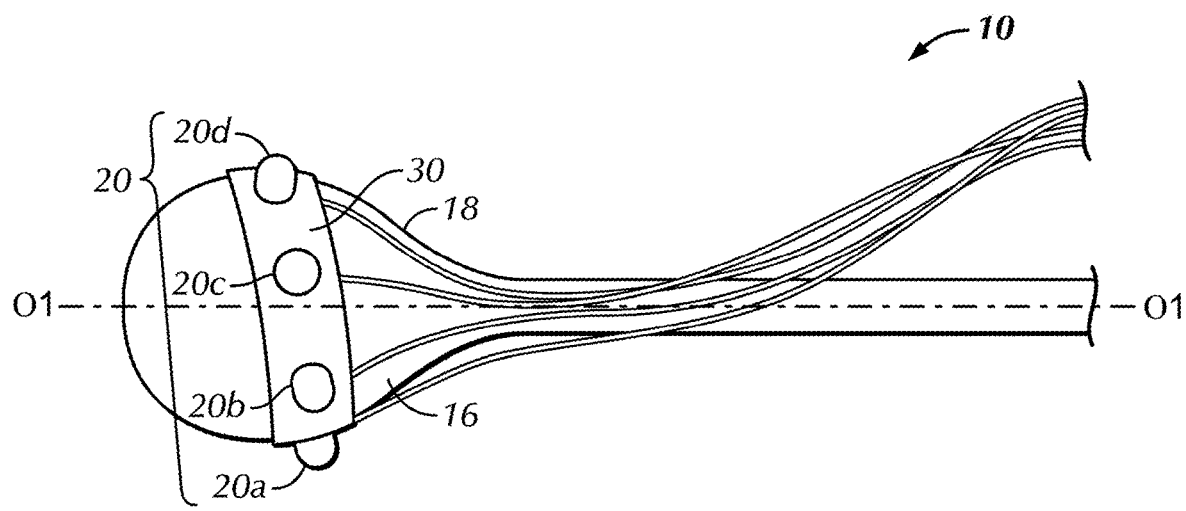
FIG. 1 is a picture of an intravaginal measurement probe in a vagina evaluation device of the present invention when viewed from the inside of the vagina (in the radial direction).
Figure 2:
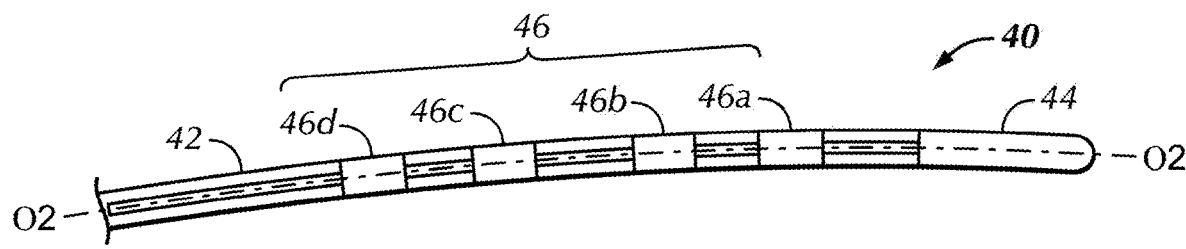
FIG. 2 is a picture of a uterine cavity measurement probe in a uterus evaluation device of the present invention using a four-electrode method when viewed from the inside of the uterine cavity (in the radial direction).

Specific embodiments of a vagina evaluation device and uterus evaluation devices of the present invention will be described below. As described above, the vagina evaluation device serves to measure an intravaginal impedance, and the uterus evaluation devices serve to measure an impedance or redox potential difference in a uterine cavity. In the specification, the vagina evaluation device is described as an intravaginal measurement probe, and the uterus evaluation devices each are described as a uterine cavity measurement probe. FIG. 1 is a picture of the intravaginal measurement probe when viewed from the inside of the vagina (in the radial direction). FIG. 2 is a picture of the uterine cavity measurement probe when viewed from the inside of the uterine cavity (in the radial direction).

As illustrated in FIG. 1, the intravaginal measurement probe 10 is configured of a substantially hollow tube member 12, and a balloon 18 in this order from right in this figure. Air can be injected into the balloon 18 through the tube member 12 by using a pump not illustrated. The balloon 18 includes a hollow air injection portion 16 that is fluidly connected to the tube member 12 on the substantially coaxial line. The air delivered in the air injection portion 16 through the tube member 12 is discharged from one or more openings (not illustrated) formed at desired positions of the balloon 18, to fill the balloon 18. A tip (left end in the figure) of the air injection portion 16 is integrally welded to the right end of the balloon 18. The tube member 12 may be coupled to the air injection portion 16 by using a coupling member 14 (see FIG. 3). In this case, the hollow tube member 12 and air injection portion 16 are coupled to each other by allowing their ends to overlap each other and fixedly wrapping around the ends with the metal coupling member 14, to deliver air in an airtight manner.

The tube member 12, the air injection portion 16, and the balloon 18 are made of a resin material such as silicone. In the example illustrated in FIG. 1, the inner diameter of the tube member 12 is 0.8 mm to 6.0 mm, and the inner diameter of the air injection portion 16 is preferably smaller than or substantially equal to the inner diameter of the tube member 12.

When filled with air, the balloon 18 expands substantially in the radial direction (a below-mentioned vagina wall direction) with respect to an axial line O1-O1. On the contrary, expansion in the axial line O1-O1 is restricted. This is due to that the tip of the air injection portion 16 is fixed to the tip of the balloon 18 as described above. FIG. 1 illustrates the expanded state. Here, a maximum expandable diameter is φ38 mm.

A cingulum-like member 30 and four electrodes 20 (20a, 20b, 20c, and 20d) are arranged on the outer face of the balloon 18 substantially at the center thereof in the axial line O1-O1 direction, and the tips of the electrodes 20 each are exposed to the outside. The cingulum-like member 30 is welded or adhered to the outer face of the balloon 18. The cingulum-like member 30 has a width that is larger than the outer diameter of each electrode 20, and extends over the electrodes 20a to 20d. The cingulum-like member 30 is made of a resin material such as silicone, and is prevented from deforming as the balloon 18 expands with air injection. The cingulum-like member 30 may be arranged on an inner face of the balloon 18. Each of the electrodes 20 is embedded into the balloon 18 from the outside via the cingulum-like member, and is welded or adhered to the balloon 18. As described in detail later, the electrodes 20a, 20b, 20c, and 20d are arranged in a line with a predetermined interval therebetween in the circumferential direction of the balloon 18, and the cingulum-like member 30 fixes the interval between the electrodes 20 irrespective of expansion of the balloon 18. As a result, in measuring the impedance using the probe, even when the amount of expansion of the balloon 18 varies according to a subject, the interval between the electrodes 20 is kept uniform.

A method of using the intravaginal measurement probe 10 illustrated in FIG. 1 will be briefly described below. In the example illustrated in FIG. 1, the balloon 18 is expanded. In fact, however, the doctor or the like inserts the probe, with the balloon 18 contracted, into the subject's vagina. After insertion, air is injected into the balloon 18 via the tube member, to expand the balloon 18. Desirably, the balloon 18 is expanded until the electrodes 20 arranged on the outer face of the balloon 18 make contact with and press the vagina wall.

After the intravaginal measurement probe 10 is inserted and then, the balloon 18 is expanded as described above, the impedance in the vagina wall is measured. The present invention adopts a four-electrode method generally used as a method of measuring impedances in the living body. Typically, according to the four-electrode method, it is essential that the interval between the electrodes 20b and 20c as a pair of voltage measuring electrodes is uniform, and the electrodes 20a and 20d as a pair of current measuring electrodes are arranged so as to sandwich the electrodes 20b and 20c therebetween substantially in the same line. Actually, a current is passed between the electrodes 20a and 20d to measure a voltage across the electrodes 20b and 20c in the same line. Thus, the current and the voltage between the electrodes 20b and 20c are measured, enabling a detector not illustrated to detect the impedance. Accordingly, as can be recognized, it is important the interval between the electrodes 20b and 20c is uniform, and the electrodes 20a to 20d are arranged substantially in the same line (one line).

The electrodes 20a, 20b, 20c, and 20d are arranged in a line in the circumferential direction of the balloon 18. Based on the Inventors' past experiences, the interval between the electrodes 20b and 20c, the interval between the electrodes 20a and 20b, and the interval between the electrodes 20c and 20d each are preferably, 6 mm. The interval between the electrodes 20a and 20b, and the interval between the electrodes 20c and 20d may be changed.

Figure 3:
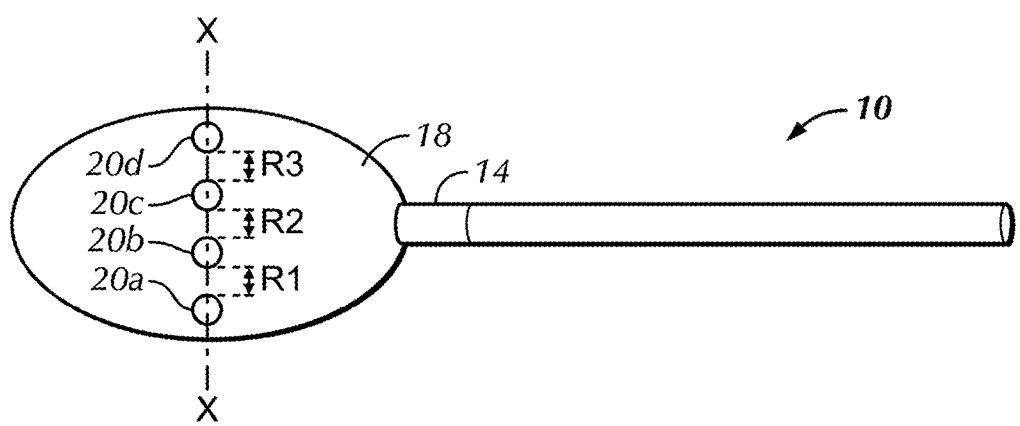
FIG. 3 is a schematic representation of the picture of the intravaginal measurement probe illustrated in FIG. 1.
Figure 4A:
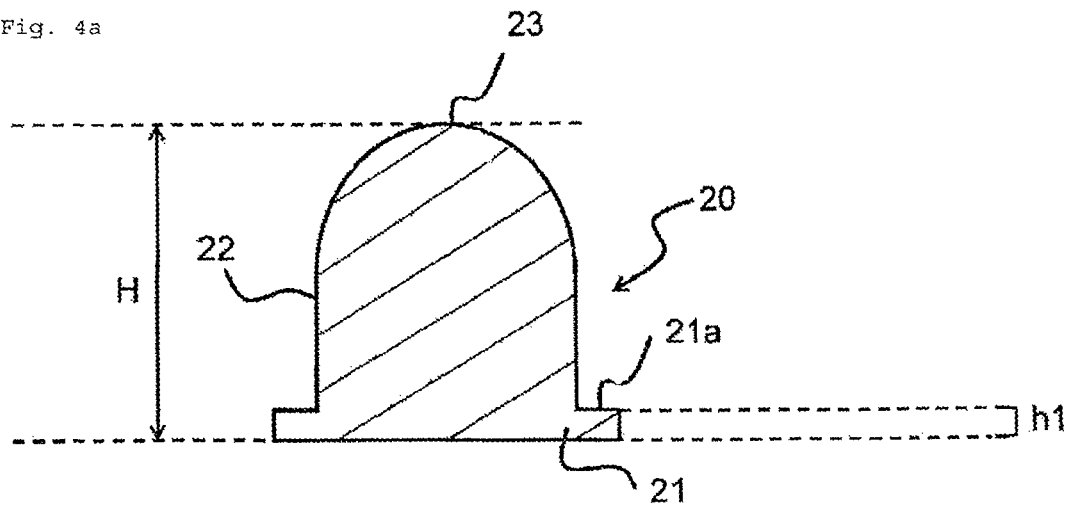
FIG. 4(a) is a schematic enlarged view of each of electrodes illustrated in FIG. 1, and illustrates the cross section of the electrode when viewed from the circumference of a balloon.
Figure 4B:
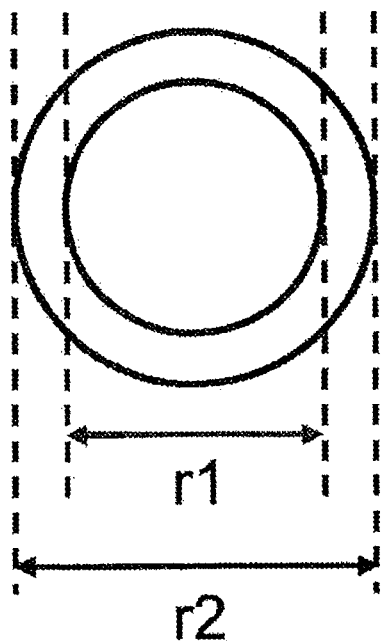
FIG. 4(b) is a schematic enlarged view of each of electrodes illustrated in FIG. 1, and illustrates each of the electrodes 20a to 20d from above (vagina wall side).

In applying the above-mentioned four-electrode method to measurement of the impedance in the vagina, the inventors (Kimura, Nakamura, Hosono) found that shape and arrangement of the electrodes in FIGS. 3 to 4 were preferable in light of anatomical specialties of the vagina of the human body. Based on the finding, FIG. 3 schematically represents the picture of the intravaginal measurement probe 10 in FIG. 1, and FIGS. 4(a) and 4(b) schematically represent the electrodes 20a to 20d. FIG. 3 illustrates the size and position of the balloon 18 expanded such that the impedance can be measured in the vaginal cavity. FIG. 4(a) is a front sectional view of the electrodes 20a to 20d when viewed from the circumference of the balloon 18, and FIG. 4(b) is a plan view of the electrodes 20a to 20d when viewed from above (vagina wall side).

As illustrated in FIG. 3, the electrodes 20a to 20d are arranged along a line X-X on the surface of the balloon 18, an interval R1 between the electrodes 20a and 20b, an interval R2 between the electrodes 20b and 20c, and an interval R3 between the electrodes 20c and 20d each are 6 mm. As illustrated in FIGS. 4(a) and 4(b), each of the electrodes 20 is integrally configured of a substantially semicircular tip 23, a cylindrical leg 22, and a disc-like flange 21, which are arranged from above in a direction of a height H of the vagina wall. A bottom of the tip 23 has the same diameter as the upper end of the leg 22 has. The flange 21 has a larger diameter than the leg 22 has, and they are concentrically constructed. In the example illustrated in FIGS. 4(a) and 4(b), the height H of the electrode is 5.5 mm, a diameter r1 of the tip 23 and the leg 22 is 5.0 mm, a diameter r2 of the flange 21 is 7.0 mm, and a height h1 of the flange is 0.5 mm. The flange 21 penetrates the surface of the balloon 18 illustrated in FIGS. 1 and 3 and is disposed therein. The upper face of a collar 21a protruding outward from the leg 22 is adhered to the inner wall face of the balloon 18 via the cingulum-like member 30. As described above, since the electrodes 20 protrude outside the balloon 18 in the vagina wall direction (upward in FIG. 3), the tip 23 and the leg 22 are exposed to the outside at the position separated from the upper face of the collar 21a by a sum of the thickness of the balloon 18 and the thickness of the cingulum-like member 30.

Next, a uterine cavity measurement probe using the four-electrode method from a second aspect of the present invention will be described. FIG. 2 illustrates the uterine cavity measurement probe including five electrodes: four impedance electrodes and one redox potential difference electrode. As illustrated in FIG. 2, the uterine cavity measurement probe 40 is configured of a substantially flexible rod-shaped member 42, a redox potential difference electrode 44, and impedance electrodes 46. The redox potential difference electrode 44, and the impedance electrodes 46a, 46b, 46c, and 46d are arranged with a predetermined interval therebetween on the surface of the rod-shaped member 42 in this order from the tip of the rod-shaped member 42 (right side in this figure). The redox potential difference electrode 44 coats a portion around an axial line O2-O2 and the tip of the rod-shaped member 42, and the impedance electrodes 46 coat a portion around the axial line O2-O2 of the rod-shaped member 42. The diameter of the rod-shaped member 42 is φ2.5 mm that is the almost same as the diameter of the uterine cavity of the human body and however, may be changed according to the diameter of the subject's uterine cavity.

A method of using the uterine cavity measurement probe 40 illustrated in FIG. 2 will be briefly described below. The uterine cavity measurement probe 40 is inserted into the subject's uterine cavity such that the redox potential difference electrode 44 and the impedance electrodes 46 make contact with the endometrium of the uterine cavity. As in the intravaginal measurement probe 10 adopting the four-electrode method, it is important that the interval between the impedance electrodes 46b and 46c is uniform, and the impedance electrodes 46a to 46d are arranged substantially in the same line (one line). The impedance electrodes 46 are arranged on the surface of the rod-shaped member 42 along the axial line O2-O2 and thus, are reliably arranged in the same line (one line). Further, the redox potential difference between the endometrium of the uterine cavity in contact with the electrode 44 and a body surface electrode can be measured with a potentiometer not illustrated, to measure the redox potential difference in the uterine cavity.

Figure 5:
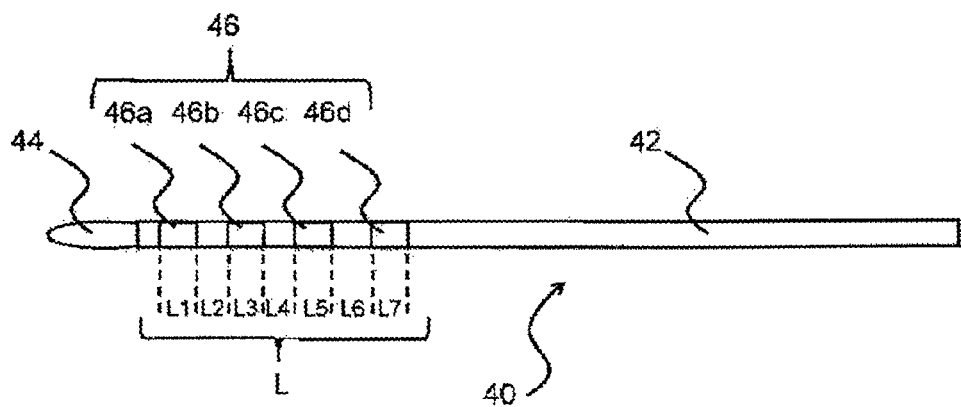
FIG. 5 is a schematic representation of the picture of the uterine cavity measurement probe illustrated in FIG. 2.

In applying the above-mentioned four-electrode method to measurement of the impedance in the uterine cavity, the inventors (Kimura, Nakamura, Hosono) found that arrangement illustrated in FIG. 5 was preferable in light of anatomical specialties of the uterine cavity of the human body. Based on the finding, FIG. 5 schematically represents the picture of the uterine cavity measurement probe 40 in FIG. 2.

As illustrated in FIG. 5, the impedance electrodes 46a, 46b, 46c, 46d are arranged on the surface of the rod-shaped member 42 in this order from the tip of the rod-shaped member 42 (left side in this figure). In FIG. 5, lengths L1, L3, L5, and L7 of the impedance electrodes 46 each are 4.0 mm, an interval L2 between the impedance electrodes 46a and 46b, and an interval L6 between the impedance electrodes 46c and 46d each are 4.0 mm, and an interval L4 between the impedance electrodes 46b and 46c is 6.0 mm.

A uterine cavity measurement probe, although not illustrated, as another embodiment using the four-electrode method from the second aspect of the present invention is different from the above-mentioned uterine cavity measurement probe including the five electrodes: the four impedance electrodes and one redox potential difference electrode only in that no redox potential difference electrode 44 is provided, failing to measure the redox potential difference. In the uterine cavity measurement probe having no redox potential difference electrode 44, the rod-shaped member 42 or the impedance electrodes 46a may be disposed in an area where the redox potential difference electrode 44 is to be arranged.

Figure 6A:
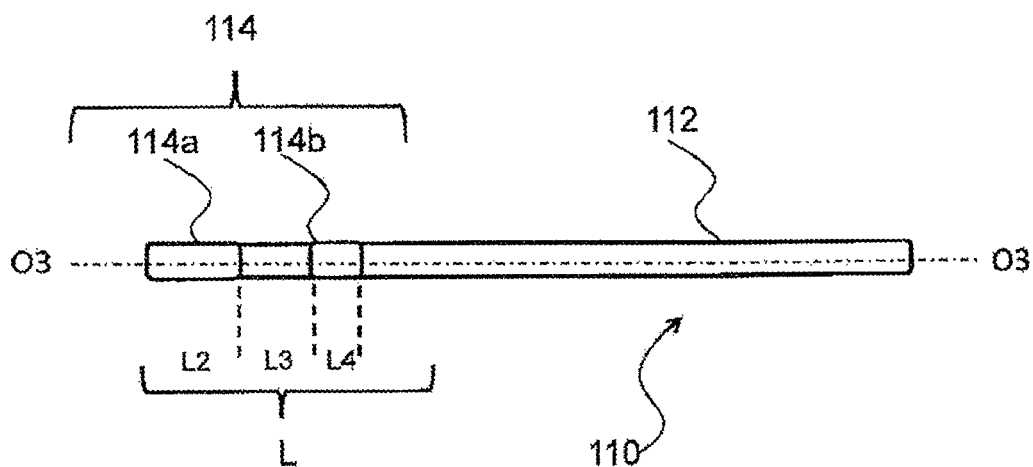
FIG. 6(a) is a schematic view of an example of the uterine cavity measurement probe in the uterus evaluation device of the present invention using a two-electrode method.
Figure 6B:
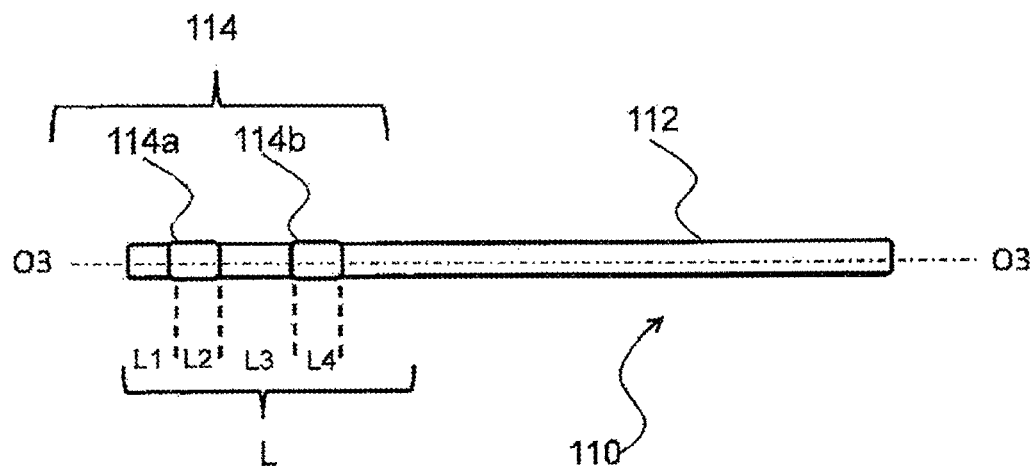
FIG. 6(b) is a schematic view of another example of the uterine cavity measurement probe in the uterus evaluation device of the present invention using the two-electrode method.

Next, a uterine cavity measurement probe adopting a two-electrode method from a third aspect of the present invention will be described. First, as illustrated in FIGS. 6(a) and 6(b), the two-electrode type uterine cavity measurement probe 110 from the third aspect of the present invention is configured of a rod-shaped member 112 and two electrodes 114a and 114b. The electrodes 114a and 114b are arranged with a predetermined interval L therebetween on the surface of the rod-shaped member 112 in this order from a tip of the rod-shaped member 112 (left side in the figures). The electrode 114a coats a portion around an axial line O3-O3 or a tip of the rod-shaped member 112, and the electrode 114b coats a portion around the axial line O3-O3 of the rod-shaped member 112. FIG. 6(a) illustrates the two-electrode type uterine cavity measurement probe 110 in which the electrode 114a coats the portion around the axial line O3-O3 and the tip of the rod-shaped member 112. FIG. 6(b) illustrates the two-electrode type uterine cavity measurement probe 110 in which the electrode 114a coats the portion around the axial line O3-O3 of the rod-shaped member 112.

The diameter of the rod-shaped member 112 is desirably, the almost same as the diameter of the uterine cavity of the human body, or may be changed according to a diameter of the subject's uterine cavity. The rod-shaped member 112 may be partially or wholly flexible.

A method of using the two-electrode type uterine cavity measurement probe 110 illustrated in FIGS. 6(a) and 6(b) will be briefly described below. The two-electrode type uterine cavity measurement probe 110 is inserted into the subject's uterine cavity to bring the electrodes 114 into contact with the endometrium of the uterine cavity. The two electrodes that are in contact with the endometrium of the uterine cavity can measure the impedance. The four-electrode method has a low grounding resistance and a high measurement accuracy. The two-electrode type uterine cavity measurement probe 110 adopts the two-electrode method for measuring the impedance between two electrodes. For this reason, the probe 110 with simple configuration in electrodes and circuit is excellent in yield rate, and can readily execute the measurement processing, achieving inexpensive and simple measurement.

In applying the two-electrode method to measurement of the impedance in the uterine cavity, the Inventors (Kimura, Nakamura, Hosono) found that widths L2 and L4 of the two electrodes 114 along the axial line O3-O3, an interval L3 between the two electrode 114, or an interval L1 between the tip of the rod-shaped member 112 and the electrode 114a were important, and especially, L1 was a predetermined distance. The predetermined distance will be described with reference to FIGS. 7 to 10.

Figure 7:
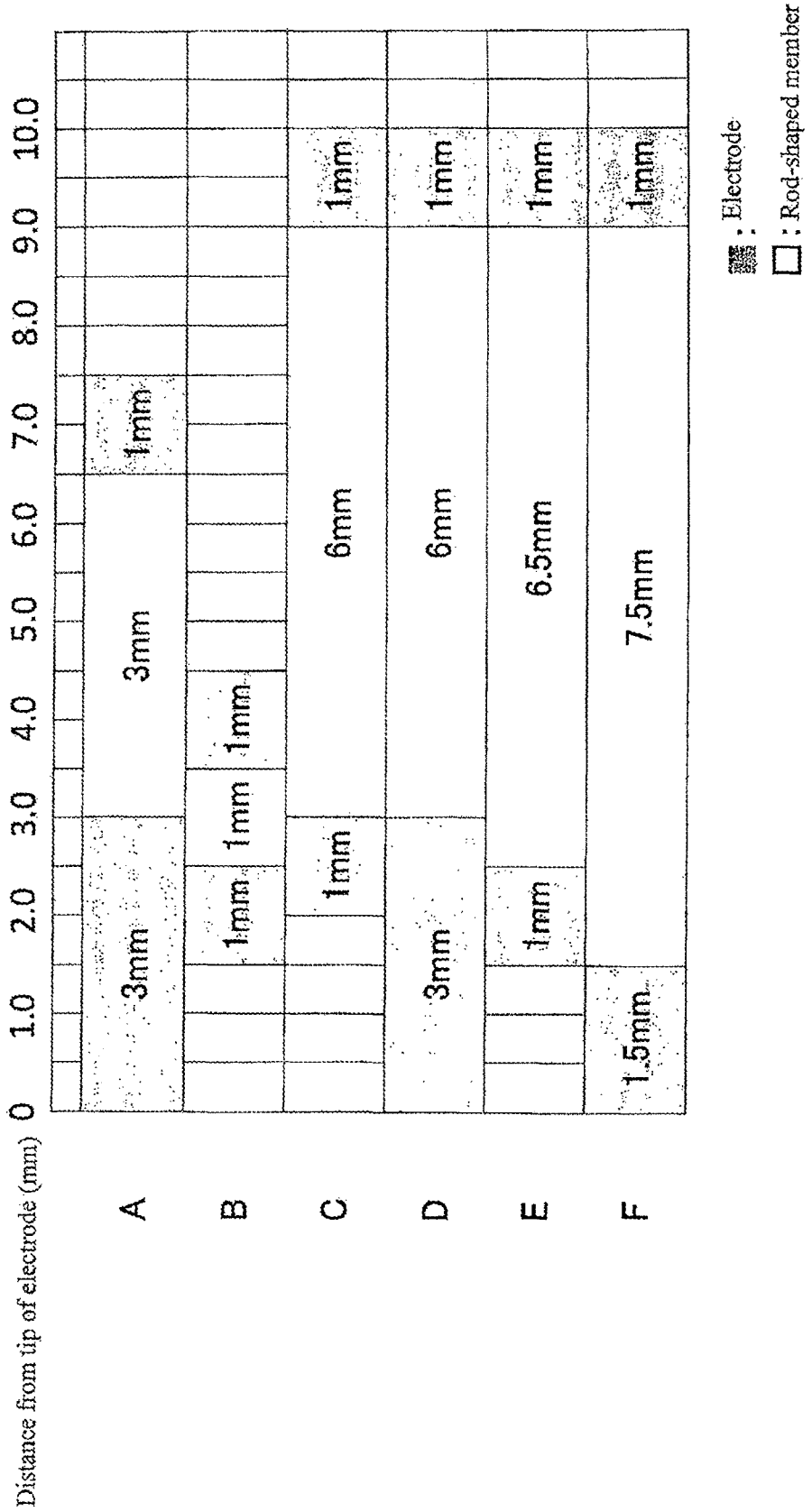
FIG. 7 is a schematic view of six types of uterine cavity measurement probes of different electrode width and intervals between adjacent electrodes in the uterus evaluation device of the present invention using the two-electrode method.

First, as illustrated in FIG. 7, the Inventors prepared six types of probes of different electrode intervals L. FIG. 7 schematically illustrates the electrode widths (L2, L4) and the electrode intervals (L1, L3) of the six types of probes A to F in the range (11 mm) from the tip to the electrode 114b. In FIG. 7, gray blocks represent the electrodes 114, white blocks represent the rod-shaped member 112, and numerals described in the blocks represent the electrode widths (L2, L4) or the electrode interval (L3). The probes has the same configuration as the two electrode type-uterine cavity measurement probe 110 illustrated in FIGS. 6(a) and 6(b) except for the electrode intervals L. As illustrated in FIG. 7, the electrode intervals L (L1, L2, L3, L4) of the probes are (0, 3, 3, 1) in the probe A, (1.5, 1, 1, 1) in the probe B, (2, 1, 6, 1) in the probe C, (0, 3, 6, 1) in the probe D, (1.5, 1, 6.5, 1) in the probe E, and (0, 1.5, 7.5, 1) in the probe F, which are represented in units of mm.

The intravaginal impedance in mature female mice were measured using the six different types of probes. Since the vaginal cavity is anatomically connected to the uterine cavity, the intravaginal impedance and the uterine endometrial impedance exhibit the same value or tendency. Therefore, the intravaginal impedance can be measured, thereby evaluating the uterine endometrial impedance, in turn, evaluating the uterus, especially, the uterine implantation capacity.

Female mice were bred with male mice. The morning when a vaginal plugging was first observed was designated as day 0.5 post coitus (p.c.). The uterine endometrial impedance was measured at day 2.5 and 4.5 p.c. If there are significantly different between day 2.5 and 4.5 p.c., it means that this parameter can reflect uterine condition. The impedance at 1 kHz was measured using a MK10-C (Muromachi Kikai Co., Ltd.). Each experimental group was examined more than 6 times. Statistical analysis was performed using the t-test. If a p-value is less than 0.05, the difference is considered to be statistical significance.

Figures 8A, 8B:
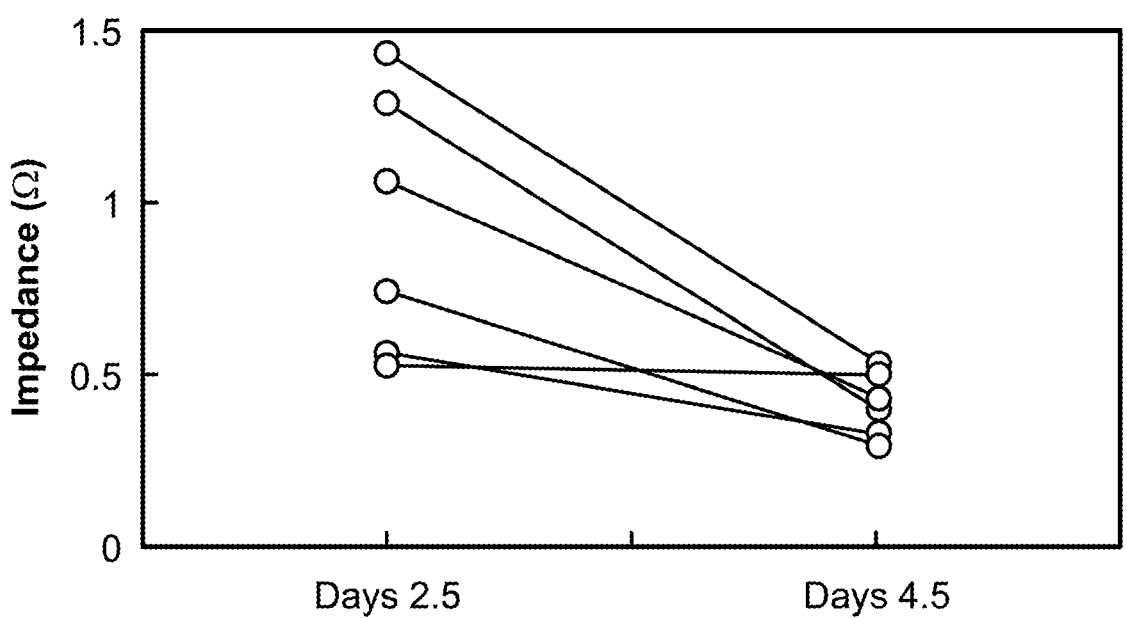
FIG. 8(a) is a table indicating impedance measurement results of mice on the gestational days 2.5 and the gestational days 4.5 using the six types of probes.
FIG. 8(b) is a graph indicating impedance measurement results of mice on the gestational days 2.5 and the gestational days 4.5 using one type of probe.

According to the test, as illustrated in FIG. 8($a$), in each of the probes A, B, C, D, and E, a significant difference between the intravaginal impedances in mice at day 2.5 and 4.5 p.c. was observed. Therefore, L3 among the electrode intervals L was 1.0 to 6.5 mm irrespective of L1 and L2, the mouse implantation progress could be accurately evaluated. FIG. 8($b$) illustrates specific experimental results of the probe B. In FIG. 8($b$), a horizontal axis indicates days, a vertical axis indicates impedance value, and six iterations are represented in 6 line segments. According to the t test (p<0.05), the significant difference between the impedance values at day 2.5 and 4.5 p.c. in mice was observed. Although specific experimental results of the probes A, C, D, E, and F were omitted, the presence/absence of substantial difference was determined in the same manner.

That is, the interval L3 between the two electrodes 114 was preferably, 1.0 to 6.5 mm.

In detail, although the probes C and D differ from each other in electrode intervals L1 and L2, both have a substantial difference. Accordingly, it can be concluded that L1, that is, whether or not the electrode 114$a$ coats the tip, L1, and L2, that is, the electrode width of the electrode 114$a$ do not have a large effect on results.

Next, intravaginal impedances of an implantation failure model mouse and a control mouse were measured using the six types of probes. The implantation failure model mouse is sterile and thus, does not become implanted. The intravaginal impedances of the implantation failure model mice at day 2.5 p.c. after crossing with a male mouse, and control mice were measured. When the intravaginal impedances have a substantial difference therebetween, it can be determined that implantation of the mice can be accurately measured. The impedances were measured using a MK10-C of Muromachi Kikai Co., Ltd., and the impedance value at 1 kHz was used as a measurement parameter. Each probe was tested six times, and a t test (p<0.05) for determining the substantial difference was performed to determine whether or not the difference between the intravaginal impedances of the implantation failure model mice and the control mice was substantial.

Figure 9:
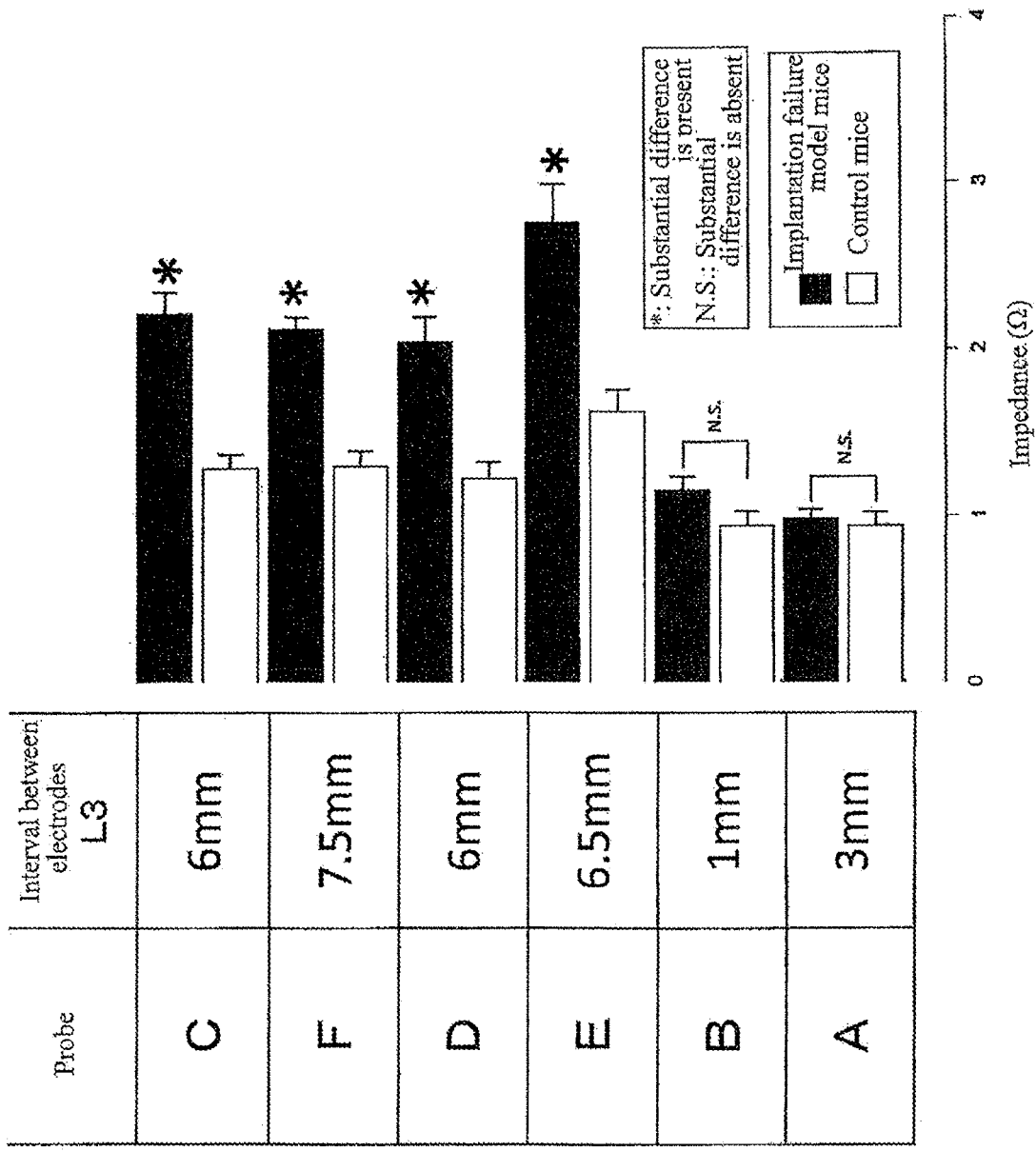
FIG. 9 illustrates measurement results of intravaginal impedances of an implantation failure model mouse and a control mouse.

FIG. 9 illustrates the results. FIG. 9 illustrates measured intravaginal impedance values of the implantation failure model mice and the control mice in a horizontal axis. In FIG. 9, black bars represent results of the implantation failure model mouse, white bars represent results of the control mice, and a letter T at a right end of each bar represent a standard error. Further, a sign "*" is expressed on right side of each of the black bars of the probes having a significant difference between the two types of measured values. As illustrated in FIG. 9, in the probes C, D, E, and F, the significant difference between the intravaginal impedances of the implantation failure model mice and the control mice was observed. Therefore, when L3 among the electrode intervals L is 6.0 to 7.5 mm, mice implantation can be accurately evaluated irrespective of L1 and L2.

That is, the interval L3 between the two electrode 114$s$ was preferably, 6.0 to 7.5 mm.

In detail, the probes A and D, or the probes B and D differ from each other only in the electrode interval L3, and only the probes E and D have a substantial difference. Accordingly, it can be concluded that L1, L2, and L4 do not have a large effect on results. Although the probes C and D differ from each other in electrode intervals L1 and L2, both have a substantial difference. Similarly, it can be concluded that L1 and L2 do not have a large effect on results.

As apparent from the above experimental results, when the interval L3 between the two electrode 114 is 6.0 to 6.5 mm, the implantation progress and implantation can be accurately evaluated, which is especially desirable.

The above-mentioned results are acquired through the experiments using the mice, and intravaginal impedances of mice and human change due to implantation in the same manner. Therefore, the two-electrode type uterine cavity measurement probe 110 of the present invention can measure the human's intrauterine impedance, thereby evaluating the uterus, in particular, the implantation capacity inexpensively, simply, or accurately.

From the above-mentioned experimental results, it is determined that the electrode width of the electrodes 114 does not have a large effect on the measured impedance values. However, when the electrode width is too large, the electrodes may be unstably mounted on the vagina wall or in the uterine cavity. Thus, desirably, the electrode width is smallest to the extent possible in consideration of yield rate. The experimental results demonstrate that the electrode width of 1 to 3 mm can properly measure the impedance.

From the above-mentioned experimental results, whether the electrode 114$a$ coats the tip of the rod-shaped member 112 (FIG. 6($a$)) and does not coat the tip of the rod-shaped member 112 (FIG. 6($b$)) does not have an effect on the measured impedance values. Accordingly, when the electrode 114$a$ does not coat the tip of the rod-shaped member 112 (FIG. 6($b$)), another member may be attached to the tip of the rod-shaped member 112 so as not to bring the tip of the rod-shaped member 112 into contact with the electrode 114$a$. In the case where the member is the redox potential difference electrode, the impedance and the redox potential difference can be simultaneously measured, thereby evaluating the uterus, in particular, the uterine implantation capacity, based on the above-mentioned two parameters.

Although not illustrated, like the above-described four-electrode type uterine cavity measurement probe provided with the redox potential difference electrode 44, the two-electrode type uterine cavity measurement probe provided with the three electrodes: the two impedance electrodes and one redox potential difference electrode, as an embodiment from the third aspect of the present invention, includes a redox potential difference electrode that coats a portion around the axial line O3-O3 and the tip of the rod-shaped member 112, so as to prevent contact with the electrode 114$a$.

Exemplary embodiments from the first to third aspects of the present invention have been described above. However, those skilled in this art could recognize that the vagina evaluation device and the uterus evaluation devices of the present invention are not limited to the embodiments, and may be modified or improved so as not to deviate from the spirit and teaching of Claims and Description.

The invention claimed is:

1. A uterine evaluation device for biological evaluation of a subject's uterus, the device comprising:
   a rod-shaped main body capable of being inserted into a uterine cavity;
   three electrodes arranged with a predetermined interval therebetween in an insertion direction of the main body, the electrodes being brought into contact with an endometrium of the uterine cavity, wherein the electrodes include a uterine redox potential difference electrode arranged entirely at the distal end of a tip of the main body in the insertion direction of the main body to measure a redox potential difference between the uterine cavity and a body surface, and two impedance electrodes arranged with a predetermined interval of 6.0 to 6.5 mm therebetween in the rear of the redox potential difference electrode in the insertion direction to measure a uterine endometrial impedance generated between the endometrium of the uterine cavity and each of the impedance electrodes;

a body surface electrode; and a measurement device configured to measure the redox potential difference between the uterine redox potential electrode and the body surface electrode, wherein the uterine redox potential electrode is electrically coupled to the measurement device, and wherein the body surface electrode is also electrically coupled to the measurement device.

2. The uterine evaluation device according to claim 1, wherein
each of the impedance electrodes is cingulum-shaped, and coats the main body around an axis of the main body.

3. The uterine evaluation device according to claim 1, wherein the measurement device comprises a potentiometer.

4. The uterine evaluation device according to claim 1, wherein the redox potential difference corresponds to a potential difference measured between the redox potential difference electrode and the body surface electrode, without electrical excitation, and wherein the impedance electrodes are arranged to measure an impedance by introducing a current into a first one of the impedance electrodes and measuring impedance between the impedance electrodes by measuring a voltage at a second one of the impedance electrodes and determining an impedance based on the measured voltage and the current.

* * * * *